United States Patent [19]

Röckseisen

[11] Patent Number: 5,707,360
[45] Date of Patent: Jan. 13, 1998

[54] TARGET APPARATUS FOR LINEARLY INSERTING AN INSTRUMENT INTO A HUMAN BODY

[75] Inventor: Armin Röckseisen, Scharnebeck, Germany

[73] Assignee: Lap GmbH Laser Applikationen, Luneburg, Germany

[21] Appl. No.: 591,418

[22] Filed: Jan. 19, 1996

[30] Foreign Application Priority Data

Jan. 26, 1995 [DE] Germany .................. 195 02 356.0

[51] Int. Cl.⁶ .................................................. A61M 5/00
[52] U.S. Cl. .................................... 604/116; 378/206
[58] Field of Search ................... 609/116; 128/653.2; 33/DIG. 21; 606/116; 378/197, 206

[56] References Cited

U.S. PATENT DOCUMENTS

| | | | |
|---|---|---|---|
| 2,455,928 | 12/1948 | Hawks | 378/206 |
| 3,748,041 | 7/1973 | Bird | 33/DIG. 21 X |
| 3,803,418 | 4/1974 | Holstrom | 378/206 X |
| 4,139,776 | 2/1979 | Hellstrom | 378/206 X |
| 4,538,289 | 8/1985 | Scheilbengraber | 378/206 X |
| 4,836,671 | 6/1989 | Bautista | 378/206 X |
| 4,930,525 | 6/1990 | Palestrant | 604/116 X |
| 4,976,019 | 12/1990 | Kitamura | 33/DIG. 21 X |
| 5,188,110 | 2/1993 | Sugimoto | 378/206 X |
| 5,308,352 | 5/1994 | Koutrouvelis | 604/116 X |
| 5,367,779 | 11/1994 | Lee | 33/DIG. 21 X |
| 5,394,616 | 3/1995 | Claxton | 33/DIG. 21 X |

FOREIGN PATENT DOCUMENTS 330 092 12/1920 Germany .
92 18 321.2 1/1994 Germany .

*Primary Examiner*—Sam Rimell
*Attorney, Agent, or Firm*—Vidas, Arrett & Steinkraus, P.A.

[57] ABSTRACT

The invention relates to a target apparatus for linearly inserting an instrument into a human body comprising a computer tomograph for determining the piercing spot and marking it, the improvement comprising: a slide which is adjustably guided above the gantry of the computer tomograph along a horizontal guide means, preferably along a transversal plane, which slide can be arrested in any position along the guide means, a laser device for producing a target mark in space, a supporting means for mounting the laser device to the slide for being pivoted about a horizontal axis such that the beam of the laser device is pivoted in a vertical plane and further comprising an angular scale attached to the slide for indicating the pivoting angle of the laser device.

10 Claims, 3 Drawing Sheets

5,707,360

TARGET APPARATUS FOR LINEARLY INSERTING AN INSTRUMENT INTO A HUMAN BODY

The present invention relates to a target apparatus for linearly inserting an instrument into a human body.

In biopsy diagnosis needles will be pierced into the body of a patient to take tissue samples from a certain part of the body or to guide instruments to some location in the body. It has become known to determine the place of the target by means of a computer tomograph (CT). It produces a virtual sectional view of the body in a number of different sectional planes. In evaluating the CT image, the place of the target may be determined and thus the piercing spot and the direction of the piercing channel may be determined. When the piercing operation cannot be performed vertically from above or horizontally from the side, because organs or bones are an obstruction, it is difficult to transmit the piercing angle which has been determined by the CT image into reality and to guide the long needle under the appropriate angle. However, when a deviation from the correct angle occurs, the place of the target is missed and the procedure has to be repeated again.

SUMMARY OF THE INVENTION

It is thus the object of the present invention to provide a target device for linearly inserting an instrument into a human body according to which the instrument may be guided under a predetermined angle towards the predetermined place of the target in a simple manner.

The object is solved by a target apparatus for linearly inserting an instrument into a human body comprising a computer tomograph for determining the piercing spot and marking it, the apparatus including a slid which is adjustably guided above the gantry of the computer tomograph along a horizontal guide means, preferable along a transversal plane, which slide can be arrested in any position along the guide means, a laser device for producing a target mark in space, a supporting means for mounting the laser device to the slide for being pivoted about a horizontal axis such that the beam of the laser device is pivoted in a vertical place and further comprising an angular scale attached to the slide for indicating the pivoting angle of the laser device.

DETAILED DESCRIPTION OF THE INVENTION

Figure 1:
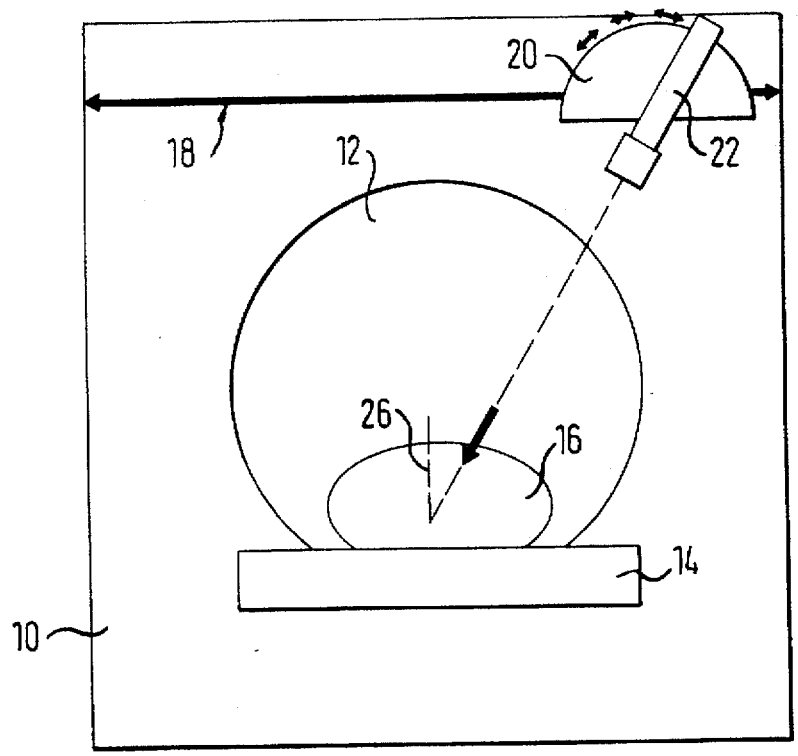
FIG. 1 is a schematic diagram of a from side of a computer tomograph including an apparatus according to the invention.

According to the invention a slide means is adjustably guided above the gantry (throughout) of the CT along a horizontal guide means, preferably along a transversal plane and the slide may be stopped and fixed at any place. The slide supports a laser device for rotating about a horizontal axis. The beam generating laser device produces a target mark, for example a point or a cross on an illuminated surface. When rotating the laser device, the laser beam will be correspondingly pivoted in a vertical plane with respect to the patient body. The slide is further provided with an angular scale which allows to read the pivoting angle of the laser device. It should be understood that the laser device may be fixed at any angular position.

The laser device is preferably formed is a unit and is pivotally attached to the slide. The laser device preferably projects a cross of lines on an illuminated surface.

Alternatively, a cross can be also projected on an illuminated surface by providing a stationary line laser having a beam plane extending in a transversal plane with respect to the patient body. A second line laser having its beam plane extending in the sagittal plane when being in the zero position, is pivotally attached to the slide.

The guide means is preferably mounted to the casing of the CT, for example being defined by a horizontal rail which is attached above the gantry. The rail can be provided with arms vertically extending with respect thereto, that arms cooperating with elongate supporting members at either side of the gantry.

The patient will be moved into and out of the CT while resting on a carriage travelling along a guide means. In starting the procedure, the slide carrying the laser device is located in the center of the guide means or the rail and the laser device is. vertically downwardly oriented in the zero position, wherein in this position the laser device generates at least one beam which projects vertically from above a cross for example onto the patient. Alternatively, there may be projected a point. As known, the sagittal line extends in the center of the carriage and the CT and the transversal line of the laser device extend parallel to the scanning plane of the CT in a fixed, but known distance. According to these lines the patient may be properly placed on the carriage. Then the patient will be moved along this line with the body portion to be scanned to the transversal plane and will be marked. The mark functions to identify the externally to be recognized reference of scanning plane and patient body. Then the patient will be scanned. The doctor selects from the CT images the appropriate scanning plane for the intervention. By considering the distance referred to, the patient resting on the carriage will be moved out until the selected scanning plane coincides with the plane of the transversal line.

The doctor then determines the piercing spot and the piercing angle by using the CT images. He determines the lateral position of the piercing spot according to prominent anatomic characteristics of the patient and marks the place of piercing. Subsequently he pivots the laser device to the predetermined angular position by pointing for example an indicator provided on the bar-shaped laser device to the preselected angle and then fixing the laser device. Then the slide carrying the pivotally adjusted laser will be moved sidewards until the laser cross hits the mark of the piercing spot. The instrument, for example a needle, must be now placed on the piercing spot such that its backside is illuminated by the laser cross. When this is obtained, the needle is now directed under the preselected angle towards the place of the target.

It should be understood that also three systems of the type referred to may be used according to which a first guide is horizontally attached and two further guides are vertically provided sidewards of the gantry to implement pivoted angles larger than 45°.

The present invention will be described in more detail as follows with reference to the drawings.

FIG. 1 shows the front side of the computer tomograph including a housing 10 and a gantry 12. A patient 16 rests on a carriage 14 which can be linearly moved through the computer tomograph. Above the gantry 12, there is provided a horizontal guide 18 along which a slide 20 may be moved. The slide 20 can be fixed to the guide 18 in any position. The slide 20 pivotally supports a bar-shaped laser device 22 which, for example, is adapted to project a cross. To this purpose, the laser device generates a pair of lines rectangularly crossing each other of which one line coincides with a transversal plane which is indicated at 24 in FIG. 2 and the other line coincides with a sagittal plane indicated at 24 in FIG. 2. As FIG. 1 shows both radiation planes referred to extending under an angle with respect to the sagittal plane of the patient which is indicated at 26 in FIG. 1.

Figure 4:
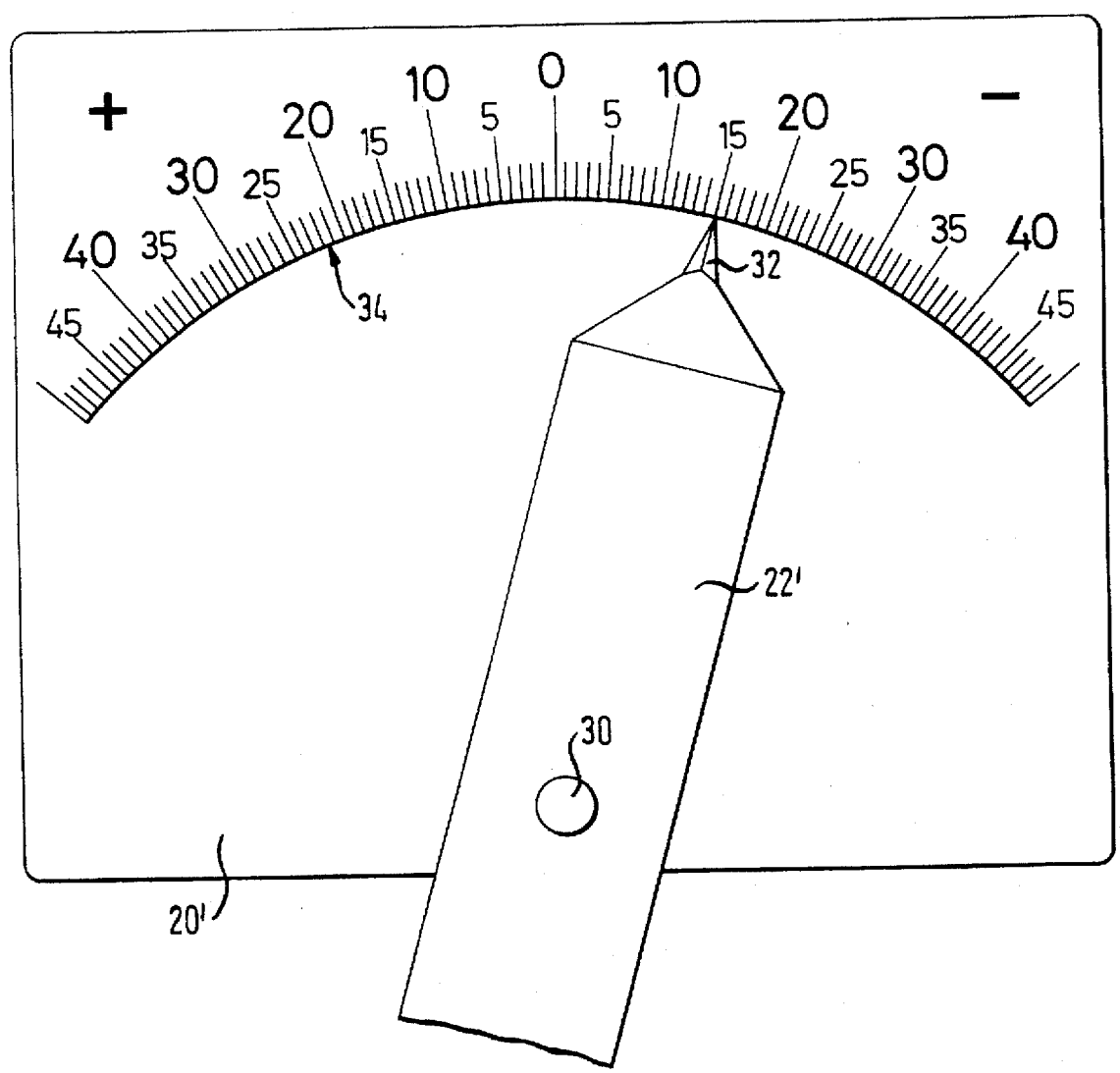
FIG. 4 shows a detail of the apparatus shown in FIG. 2.

FIG. 4 shows an alternative embodiment of a slide 20' including a laser device 22' which is pivotally supported at 30 about a horizontal axis of the slide 20'. The laser device 22 may be arrested in any angular position. The laser device 22' includes a tip provided at its rearward end 32 which tip cooperates with a scale 34 provided on the slide 20'. The scale allows to read the angular position of the laser device 22'.

As already referred to, the piercing spot of a biopsy needle for example on the patient body is determined by means of the CT and is marked on the skin by the doctor. The doctor further knows from the CT images the angle under which the instrument must be held or, respectively, guided in order to move the instrument to the place of target without affecting bones or other organs of the patient. The angular position is adjusted by the doctor in adjusting the laser device 22 or 22' to the predetermined angle and then fixing the laser device. Before that the patient has been moved out of the computer tomograph sofar until the mark made on the body coincides with the transversal plane 24 of the laser device 22. Subsequently, the slide 20 or 20' is moved along the guide 18 until also the sagittal plane 24 coincides with the mark. Now, the instrument has to be held and guided such that the cross of the laser device is projected onto its rearward end.

Figure 2:
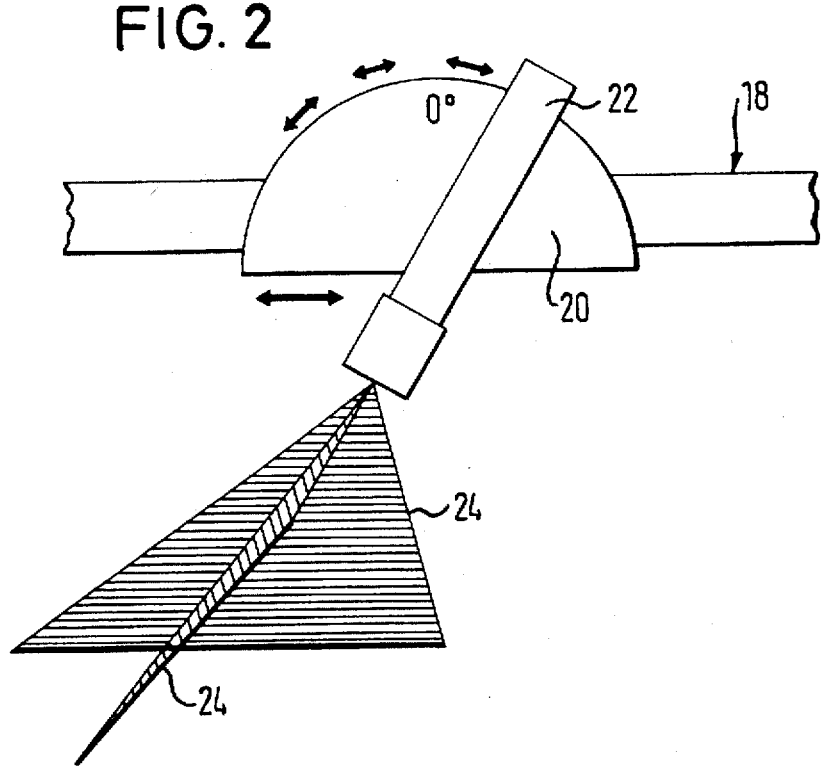
FIG. 2 shows a detail of the apparatus of FIG. 1.
Figure 3:
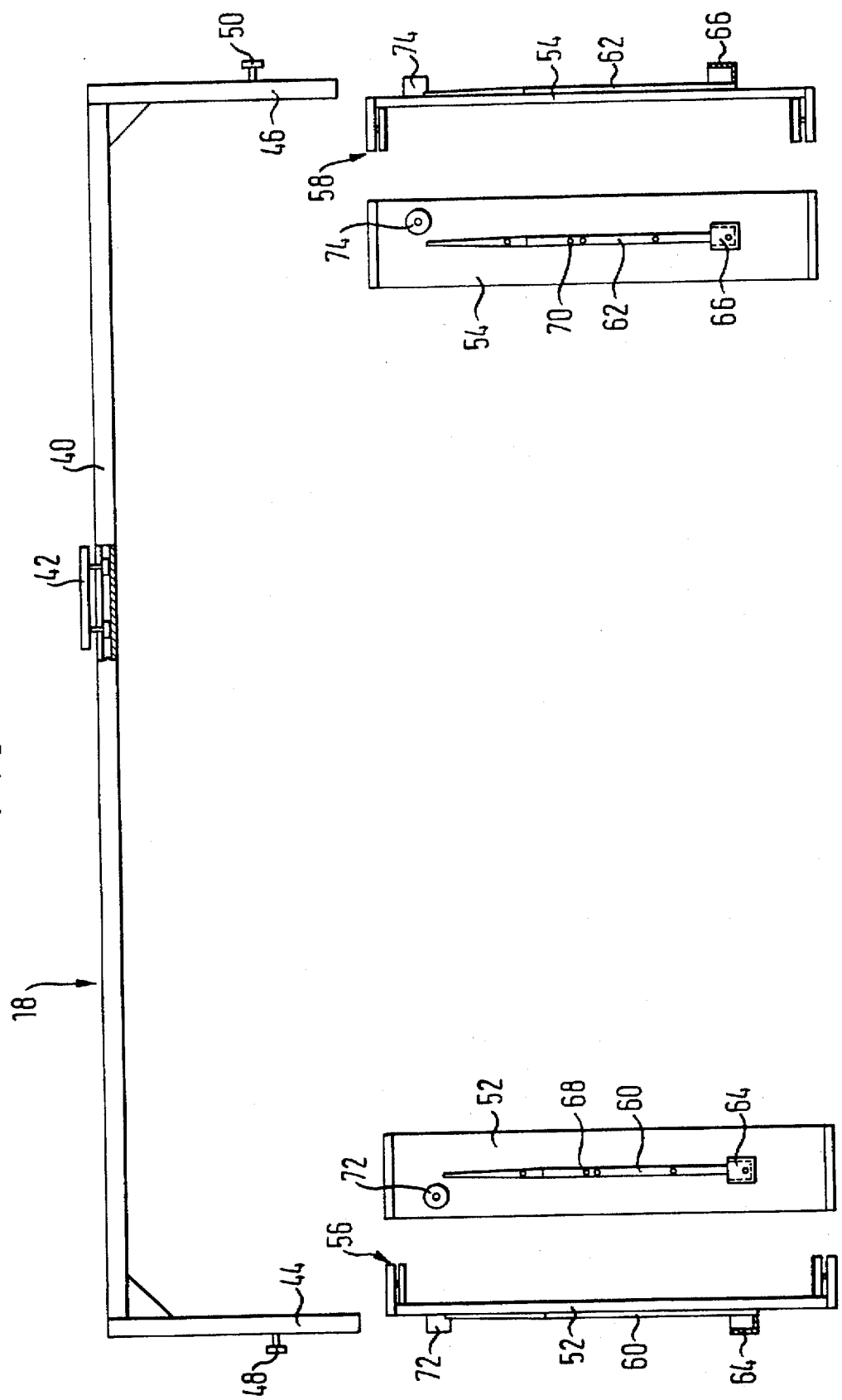
FIG. 3 is a front view of part of the apparatus shown in FIG. 1.

FIG. 4 shows how the target apparatus shown in FIGS. 1 to 3 may be mechanically implemented. The guide means 18 is formed by a rail 40 along which a slide 42 is precisely guided. Details of the guide means need not to be described. Both ends of the rail 40 are provided with vertically suspending arms 44, 46 to which outer sides a locking bolt 48, 50 each is mounted. The locking bolts are biased by springs to be urged back to the original position after being pulled out by hand.

At either side of the gantry 12, a mounting plate 52, 54 is attached to the housing 10. FIG. 3 shows a sideview of the mounting plate 52, 54 as mounted to the housing of the CT and a front view of the mounting plate. Each mounting plate 52, 54 is provided with a clamping means 56, 58 for securing to the housing in a parallel adjustment thereto. The outer side of each plate 52, 54 carries a guide rail 60, 62, the upper end thereof being ramp-shaped and gradually upwardly sloping in height as well as the width thereof gradually increasing. This ramp-shaped portion will be inserted into a complementary profile (not shown) of the arms 44, 46. The outer side in the lower portion thereof is further provided with a receiving portion 64, 66 for the arms 48, 50. The rail 60, 62 is provided with a bore 68, 70 receiving the locking bolt 48, 50 above referred to. Thus the arms 44, 46 are positioned in a proper orientation. Accordingly, the guide means 18 is precisely positioned in space. Finally, a roller 72, 74 each is rotatably supported in the upper portion sidewards of the rails 60, 62. The rollers facilitate inserting the arms 44, 46 into the mounting plate.

I claim:

1. A target apparatus for guiding the insertion of an elongated instrument comprising a front end and a back end into a human body comprising:
    a) a computer tomograph having a gantry for detecting a spot on said human body where said elongated instrument is to be pierced into said human body; and
    b) a horizontal guide means above said gantry and a slide movable along said guide means, said guide means having arresting means to arrest said slide in any position along said guide means, said slide comprising a support means thereon, said support means retaining a laser device, said laser device generating at least one laser beam and said at least one laser beam projecting a point or cross on a surface illuminated along a line intersecting with said detected spot, and said laser device being supported for rotation about a horizontal axis so that the at least one laser beam of said laser device is moved in a vertical plane, said slide further comprising an angular scale for indicating the angle of said laser device with respect to said guide means.

2. The target apparatus of claim 1, wherein the laser device generates at least one beam, said at least one beam projecting a cross on a surface illuminated.

3. The target apparatus of claim 2, comprising a first line laser which is mounted stationary and which emits a first beam extending in a transversal plane, and a second line laser which is pivotally mounted on the slide and which emits a second beam extending in the sagittal plane, the first and second beams projecting a cross on an illuminated surface.

4. The target apparatus of claim 1, wherein the laser device is bar-shaped and pivotally mounted on said support means, the laser device further comprising a beam emitting end and a pointed end opposite said beam emitting end, said pointed end cooperating with said angular scale to indicate the angle of said laser device with respect to said guide means.

5. The target apparatus of claim 1, wherein the computer tomograph further comprises a housing and said guide means is mounted on said housing.

6. The target apparatus of claim 5, wherein the guide means comprises a horizontally extending rail mounted on said housing above said gantry.

7. The target apparatus of claim 6, further comprising elongate mounting profiles attached to said housing and vertically extending arms mounted on the ends of said rail, said arms cooperating with said elongate mounting profiles.

8. The target apparatus of claim 7, further comprising a mounting means wherein the mounting means comprises a plate carrying a guiding ledge having a ramp-shaped profile increasing downwardly and away from said plate and wherein said arms include a profile complementary to said guiding ledge and a locking bolt cooperating with a locking bore in said guiding ledge each.

9. The target apparatus of claim 8, wherein said mounting means are adjustably attached to the housing.

10. The target apparatus of claim 1, wherein the slide means is adjustably guided along the horizontal guide means along a transverse plane.

* * * * *